United States Patent

Matsunaga et al.

[11] 3,980,713
[45] Sept. 14, 1976

[54] STYRYL COMPOUNDS AND PROCESS FOR PRODUCING THE SAME

[75] Inventors: Daisaku Matsunaga, Yono; Mitsukuni Sumitani, Chuo Soka, both of Japan

[73] Assignee: Nippon Kayaku Co., Ltd., Tokyo, Japan

[22] Filed: May 17, 1973

[21] Appl. No.: 361,127

[30] Foreign Application Priority Data
May 19, 1972 Japan.............................. 47-49120

[52] U.S. Cl............................... 260/612 R; 8/1 W; 260/505 R; 260/556 AR; 260/556 S; 260/613 A; 260/668 F
[51] Int. Cl.²........................................ C07C 43/20
[58] Field of Search......... 260/668 F, 668 C, 666 P, 260/666 PY, 612 R, 613 A

[56] References Cited
OTHER PUBLICATIONS

Krasovitskii, "Chem. Abstracts", vol. 66, (1967), p. 115492s.
Siegrist "Chem. Abstracts" vol. 71, (1969), p. 71927j.

*Primary Examiner*—James O. Thomas, Jr.
*Assistant Examiner*—A. Siegel
*Attorney, Agent, or Firm*—Russell & Nields

[57] ABSTRACT

This invention relates to compounds which are valuable as a fluorescent brightener and a novel process for producing the same.

The present invention is based on the following discoveries made by the inventors:

In the presence of a palladium catalyst and a base at an elevated temperature, 1 mole of a compound of the formula, $$X-A-X \qquad (1)$$

is reacted with 2 moles, in total, of one or two kinds of compounds selected from the group consisting of a styrene derivative having the formula,

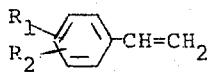

(2)

and, thereby a compound of the formula,

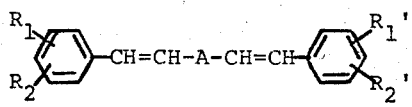

(3)

is obtained at a high yield, wherein, in the formula (1), X represents iodine or bromine, and A represents a bivalent radical selected from the group consisting of compounds of the formula,

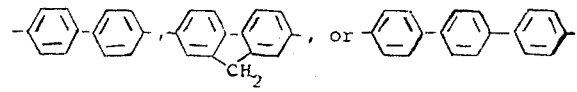

and wherein, in the formula (2), $R_1$ represents a substituent selected from the group consisting of hydrogen, chlorine, lower alkyl, methoxy, ethoxy, sulfonic acid radical or the salts thereof, sulfonamide radical, and lower-alkyl-substituted sulfonamide radical, and $R_2$ represents a substituent selected from the group consisting of hydrogen, chlorine, lower alkyl, sulfonic acid radical or the salts thereof, sulfonamide radical and lower-alkyl-substituted sulfonamide radical, and wherein, in the formula (3), A represents the same as in the formula (1), $R_1$ and $R_1'$ may be the same or different, each denoting the same as $R_1$ in the formula (2); $R_2$ and $R_2'$ may be the same or different, each denoting the same as $R_2$ in the formula (2).

3 Claims, No Drawings

STYRYL COMPOUNDS AND PROCESS FOR PRODUCING THE SAME

BACKGROUND OF THE INVENTION

Two processes are disclosed in South African Pat. No. 68,06,288 wherein (i) benzaldehyde-o-sulfonic acid is condensed with a compound of the formula,

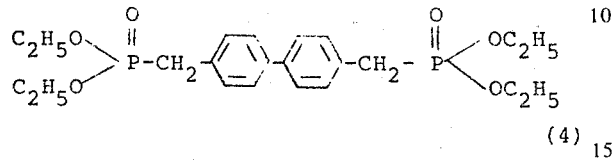

which has been obtained by reacting 4,4'-bischloromethylbiphenyl with triethylphosphite, to thereby obtain a compound of the formula,

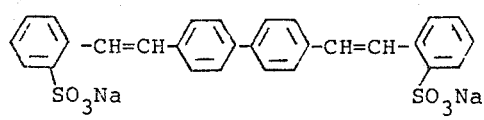

and
(ii) an aldehyde of the formula,

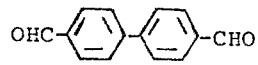

is condensed with a compound of the formula,

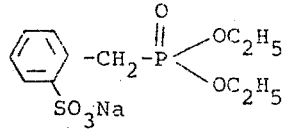

which has been obtained by reacting triethylphosphite with benzylchloride-o-sulfonic acid.

However, the monochloromethyl biphenyl, which is produced as a by-product at the time of producing 4,4'-bischloromethylbiphenyl through bischloromethylation of biphenyl, is irritative to the skin, such that the handling and production thereof results in difficulties coupled with the offensive odor of triethylphosphite which leads to a further complicated handling problem. In addition, the benzaldehyde-o-sulfonic acid is relatively costly starting material. With the other process referred to above, there are experienced the same problems in the production of the compound of the formula (6), and in addition, the compound of the formula (7) is also costly.

DETAILED DESCRIPTION OF THE INVENTION

In contrast thereto, according to the process of the present invention, the styrene sulfonic acid is obtained from styrene, which is a starting material available at a lower cost. Moreover, the styrene sulfonic acid is a mixture consisting essentially of p- and o- components, and those mixtures rich in the o- type component can be separated therefrom economically. The styrene sulfonic acid is condensed with 4,4'-diiodobiphenyl at a high yield in the presence of a base, while using a catalyst such as palladium black, to obtain a compound of the formula,

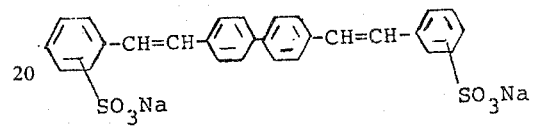

(the principal components are the same as those of formula (5)). The iodine thus used can be easily recovered from the condensed filtrate as iodide or iodine. Although the palladium black is a highly expensive compound, the amount used is extremely little and can be recovered practically completely, thus permitting the reuse thereof without particular treatment. It is for these reasons that the process of the present invention is highly evaluated. In addition, it is difficult to produce the compounds of the following formulae (useful as brighteners) by applying the process of said South African patent correspondingly

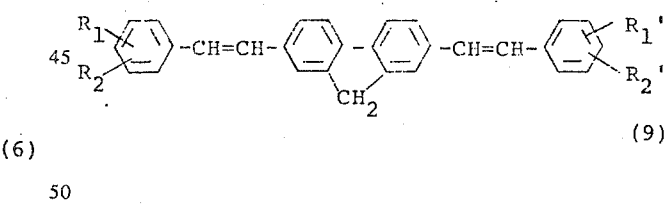

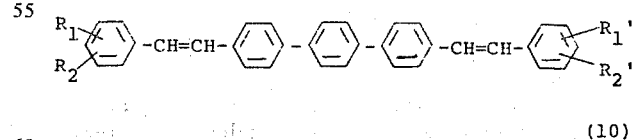

wherein $R_1$, $R_2$, $R_1'$, $R_2'$ denote the same as in the formula (3). However, the present invention permits the production of the aforesaid compounds in an economical manner with ease. The compounds of the formula (1) used as a starting material, according to the present invention can be obtained through iodinization or brominization of biphenyl, fluorene or p-terphenyl. The compounds of the formula (2) used as another starting material, can be obtained through (a) dehydrogenation of ethylbenzenes of the formula,

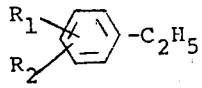

(11)

(wherein $R_1$ and $R_2$ denote the same as in the formula (2)) or through (b) elimination of hydrogen chloride or hydrogen bromide of the compounds of the formula,

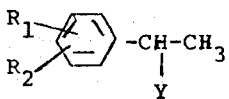

(12)

or

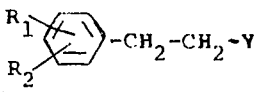

(13)

(wherein, in the formulae (12) and 13), Y represents chlorine or bromine and $R_1$ and $R_2$ denote the same as in the formula (2)), or otherwise through (c) reacting ethylene with the compounds of the following formula in the presence of palladium catalyst and a base,

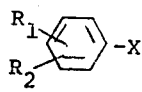

(14)

(wherein $R_1$ and $R_2$ denote the same as in the formula (2)).

Included among the palladium catalysts employable in the present invention are bivalent palladium salts such as palladous chloride, palladous acetate, or palladous sulfate, and palladium adsorbed in a carrier such as diatomaceous earth, or active carbon, and palladium black. The amount of palladium catalyst to be used is preferably at a mole ratio of 0.0002 to 2 to that of the compound of the formula (1), while a small amount of copper salt or iron salt may be used in combination therewith.

Preferably, included among the bases used in the present invention are, in general, inorganic and organic bases, particularly relatively weak inorganic bases such as potassium acetate, sodium acetate, potassium bicarbonate, sodium bicarbonate, potassium carbonate, sodium carbonate, or calcium hydroxide, and organic bases such as trimethylamine, triethylamine, tributylamine, pyridine, piperidine, N-methylpiperidine or 1,4-diazabicyclo [2.2.2]-octane (DABSCO). Alternatively, more than two kinds of those may be used in combination therewith. The amount to be used is preferably at a mole ratio of 2 to 4 to the compound of formula (1).

Included among the reaction solvents are generally alcohols, such as methanol, ethanol, n-propyl alcohol, iso-propyl alcohol, n-butyl alcohol, iso-butyl alcohol, iso-amyl alcohol, ethyleneglycol, propyleneglycol, methylcellosolve, ethylcellosolve, butylcellosolve, diethyleneglycol, diethyleneglycolmonomethylether, diethyleneglycolmonoethylether, in addition to dimethylformamide, dimethylacetamide, dimethylsulfoxide, hexamethylphosphoramide, dioxane, acetone, methylethylketone. Inactive solvents such as benzene, toluene, xylene, chlorobenzene, or o-dichlorobenzene may be used in combination therewith.

The reaction temperature should preferably be in the range from 50° to 200°C, particularly from 120° to 160°C.

A compound of the formula (2) is reacted at a mole ratio of 1:1 with the compound of the formula (1) at a temperature of about 120°C, after which the product thus obtained is reacted at a mole ratio of 1:1 at a temperature of about 160°C with another kind of compound of the formula (2) thereby to obtain a compound of the unsymmetrical formula (3).

Typical of the compounds of the formula (2) are: styrene, 2-methylstyrene, 3-methylstyrene, 4-methylstyrene, 4-ethylstyrene, 4-t-butylstyrene, 2.4-dimethylstyrene, 2-methyl-4-t-butylstyrene, 2-chlorostyrene, 3-chlorostyrene, 4-chlorostyrene, 2.4-dichlorostyrene, 2.5-dichlorostyrene, 3.4-dichlorostyrene, 2-methoxystyrene, 3-methoxystyrene, 4-methoxystyrene, 4-ethoxystyrene; styrene-2-sulfonic acid, styrene-3-sulfonic acid, styrene-4-sulfonic acid, styrene-2.4-disulfonic acid, styrene-2.5-disulfonic acid, styrene-3.4-disulfonic acid, styrene-3.5-disulfonic acid, 2-methylstyrene-3-sulfonic acid, 2-methylstyrene-4-sulfonic acid, 3-methylstyrene-2-sulfonic acid, 3-methylstyrene-4-sulfonic acid, 4-methylstyrene-2-sulfonic acid, 2-ethylstyrene-5-sulfonic acid, 4-methylstyrene-3-sulfonic acid, 2-chlorostyrene-4-sulfonic acid, 2-chlorostyrene-5-sulfonic acid, 3-chlorostyrene-6-sulfonic acid, 4-chlorostyrene-2-sulfonic acid, 2-methoxystyrene-5-sulfonic acid, 3-methoxystyrene-4-sulfonic acid, 4-methoxystyrene-3-sulfonic acid, 4-ethoxystyrene-3-sulfonic acid and the salt thereof; styrene-2-sulfonamide, styrene-4-sulfonamide, styrene-2.4-disulfonamide, styrene-3.5-disulfonamide, N-methylstyrene-2-sulfonamide, N-methylstyrene-4-sulfonamide, N-ethylstyrene-4-sulfonamide, N-isopropylstyrene-4-sulfonamide, N.N-dimethylstyrene-2-sulfonamide, N.N-dimethylstyrene-4-sulfonamide, N.N-di-n-butylstyrene-4-sulfonamide, N.N-dimethylstyrene-2.4-disulfonamide, 4-vinyltoluene-3-sulfonamide, and 4-chlorostyrene-2-sulfonamide.

Some of the compounds obtained according to the process of the invention are already known to be fluorescent brighteners. However, certain other compounds obtained according to the process of the invention are novel compounds. Such novel compounds are compounds of the formula,

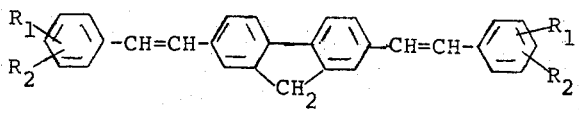

wherein $R_1$, $R_1'$, $R_2$ and $R_2'$ denote the same as in the formula (3) and compounds of the formula,

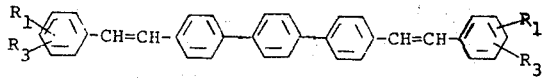

wherein $R_1$ and $R_1'$ denote the same as in the formula (3) and $R_3$, $R_3'$ represent a substituent selected from the group consisting of sulfonic acid radical or the salt thereof, sulfonamide radical and lower alkyl substituted sulfonamide radical, and are likewise employable as a fluorescent brightener agent for materials made of the following various kinds of organic materials:

1. Natural organic materials such as cellulose or protein. For instance, cotton, wool, silk, linen, leather, pulp, paper, etc.
2. Semi-synthetic organic materials, such as cellulose esters, regenerated cellulose, casein plastics, for instance, cellulose acetate, viscose, rayon, staple fiber, etc., and
3. Synthetic organic materials, such as polyesters, polyamides, polyacrylonitriles, polyolefine, polyvinylchloride, polystyrene, acrylonitrile-butadiene-styrene copolymer (ABS resin), polyurethanes, melamine resin, phenol resin.

The amount of brightener may vary a great deal and in fact, may range from 0.0001 to 1.0%, preferably 0.01 to 0.2% based on the weight of the good.

In other words, the other novel compounds of the invention are referred to above can be used for fibers, fabrics, textiles, film, sheet, shaped articles, paint, ink etc., made of the above mentioned materials.

For instance, in the case of compounds such as a substantially water insoluble material of those of the formula (3), they may be used for such a purpose by applying correspondingly the conventional processes such as dip dyeing, carrier dyeing, high temperature dyeing, pad-steam dyeing, thermosol dyeing processes, while preparing an aqueous dispersion with the aid of a suitable dispersing agent or an organic solvent miscible with water.

Furthermore, in the case of a compound containing a sulfonic acid radical, an aqueous solution treatment can be applied, immediately followed by conventional dyeing processes, such as dip dyeing, or dyeing in combination with the resin treatment, for example, a thermofix continuous dyeing process as in the case with a polyamide fiber.

Alternatively, the aforesaid fluorescent whitening treatment can be simultaneously carried out within a single bath, coupled with other treatments, such as chemical bleaching treatment.

On the other hand, a compound of the formula (3) can be used in combination with a detergent, while permitting simultaneous or combined use of refining and fluorescent whitening steps or simultaneous use of a fluorescent whitening treatment with washing by using a detergent, to which has been added a fluorescent brightener.

Furthermore, there can be obtained a copolymer which has been whitened by adding the same prior to the polymerization of the organic polymer, while fiber, film, sheet, shaped article, etc. may be whitened according to the processes such as the one by which the same is added into the spinning bath before spinning at the time of production of fibrous materials, the one whereby the same is added before or during shaping treatment of a film and sheet or shaped article, or the one which is applicable to a solution of a fluorescent brightener.

With these whitening treatments, other fluorescent brighteners may be used to achieve desired tints and a combined effect.

Alternatively, the combined use with other dyes or pigments may be used for the purpose of achieving a clear coloring effect.

Still furthermore, a compound of the formula (3) may be used as beauty aids such as a sunburn preventive cream and a scintillater.

EXAMPLE 1

Added to 100 ml of methylcellosolve were 8.4 g of 2,7-diiodo-fluorene, 4.6 g of styrene, 6 g of potassium acetate and 0.015 g of palladous chloride and the mixture was stirred with refluxing for 15 hours, followed by cooling, filtration, washing and drying, in sequence. Then followed an extraction step for separating the catalyst from the cake thus obtained, using a Soxhlet extractor and using 250 g of xylene as a solvent. The xylene extract was cooled, and the crystals thus precipitated were filtered and dried, thus obtaining a compound of the following formula, the amount thereof being 6.5 g:

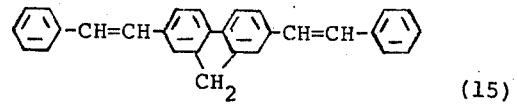

(15)

In the case of recrystallization from dimethylformamide, there can be obtained bright yellow needle crystals having a melting point of 315° to 318°C.

$C_{29}H_{22}$ = calculated: C 94.01%, H 5.99%; found: C 93.85%, H 5.81%.

The extraction residue from the Soxhlet extractor was the palladium which had been used as the catalyst and which hence can be used after treatment or in tact.

Example of the production of 2,7-diiodofluorene used as a starting material

Added to 100 ml of glacial acetic acid and 25 ml of water were 16.6g of fluorene, 25.4g of iodine, 31g of potassium persulfate, 7.2g of concentrated sulfuric acid and 20 ml of carbon tetrachloride and the mixture was stirred with refluxing for 10 hours. 3g of potassium persulfate was added thereto for further reaction for three hours, followed by cooling, filtration, washing and drying, in sequence, after whih there was obtained a crude product of 41g of 2,7-diiodofluorene having a melting point of 203°–207°C.

Recrystallization from 70 ml of chlorobenzene furnished light yellow needle crystals melting at 212° to 214°C.

Reactions were carried out similar to those of the present Example 1 and thus compounds as expressed in the following formula were obtained:

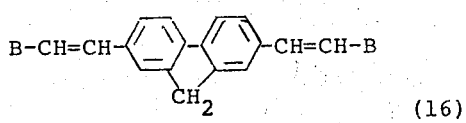

(16)

Those are enumerated as follows:

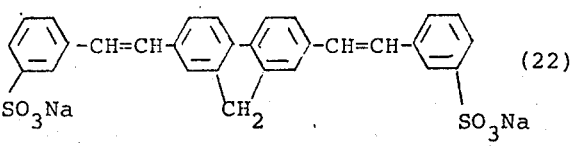

(22)

γ max = 373mμ(In 50% aqueous pyridine solution)

The sodium styrene-m-sulfonate which was used as a starting material could be produced as follows:

Added to 300 ml of autoclave were 150 ml of dimethylformamide, 25 g of sodium iodobenzene-m-sulfonate, 11 g of sodium acetate and 0.01 g of palladium black, after which ethylene was introduced therein under a pressure of 15 kg/cm$^2$ for reaction for 3 hours at a temperature of 130°C. After cooling, the content was washed out with 200 ml of water and filtered to recover the palladium black. The filtrate was evaporated under a reduced pressure for drying and then 100 ml of methanol was added thereto, followed by boiling, cooling, and filtration to thereby obtain a crude product. The crude product thus obtained was extracted with 150 ml of methylcellosolve so as to remove the solvent by

| Number of formula | B | Melting Point | Color of Crystal |
|---|---|---|---|
| (17) | CH$_3$-⟨⟩- | 324–326°C | Yellow |
| (18) | CH$_3$O-⟨⟩- | Over 330°C | Orange Yellow |
| (19) | tert-C$_4$H$_9$-⟨⟩(CH$_3$)- | 212–217°C | Yellow |
| (20) | Cl-⟨⟩(Cl)- | 230–232°C | Light Yellow |
| (21) | CH$_3$-⟨⟩-* | 281–312°C | Yellow |

*(m.p mixture)

EXAMPLE 2

Added to 50 ml of ethyleneglycol were 8.3 g of sodium styrene-m-sulfonate, 6.3 g of diiodofluorene, 4.5 g of potassium acetate, and 0.01 g of palladium black and the reaction was carried out for 5 hours at a temperature of about 160°C. After cooling, 70 ml of methanol was added with agitation for 30 minutes, followed by filtration and washing with methanol. The cake thus obtained was from 50% methylcellosolve aqueous solvent to obtain light yellow crystals the compound of the following formula:

distillation under reduced pressure thereby obtaining a refined product of 13.5 g.

Reactions were carried out similar to those of the present Example 2, and there were obtained compounds of the following formula:

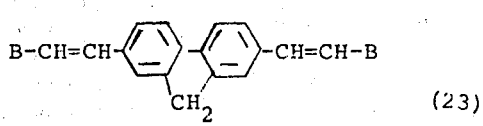

(23)

Those compounds are enumerated as follows:

| Number of formula | B | λ max | Color of Crystal |
|---|---|---|---|
| (24) | ⌬-SO₃Na | 376 | Yellow |
| (25) | KO₃S-⌬- | 374 | Light Yellow |
| (26) | CH₃-⌬(SO₃Na)- | 377 | Light Yellow |
| (27) | NaO₃S-⌬(C₂H₅)- | 375 | Yellow |
| (28) | NaO₃S-⌬-OCH₃ | 388 | Reddish Yellow |
| (29) | C₂H₅O-⌬-SO₃Na | 390 | Orange Yellow |
| (30) | Cl-⌬-SO₃Na | 376 | Light Yellow |
| (31) | NaO₃S-⌬-SO₃Na | 376 | Yellow |
| (32) | NaO₃S-⌬-SO₃Na | 375 | Yellow |

EXAMPLE 3

Added to 100 ml of n-butylalcohol were 8.4 g of 2.7-diiodofluorene, 8.1 g of styrene-4-sulfonamide, 6 g of sodium acetate, and 0.0054 g of palladous chloride, while being refluxed for reaction for 20 hours under heat. After cooling, there followed filtration and washing with 20 ml of methanol and drying. Subsequently, extraction was carried out by using a Soxhlet extractor and using 200 ml of pyridine as a solvent. The pyridine extract was cooled, filtrated and dried, and then there was obtained a compound of the following formula, the amount thereof being 8.9 g;

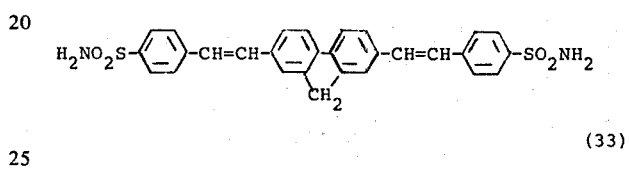

(33)

When recrystallized from dimethylformamide, there was obtained light yellow, scaly crystals having a melting point of over 330°C.

C₂₉H₂₄N₂O₄S₂ = calculated: N 5.31%, S 8.23%; found: N 5.19%, S 8.27%.

Reactions were carried out similar to those of the present Example 3, thus obtaining compounds of the following formula:

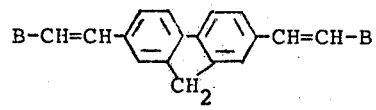

(34)

Those are enumerated as follows:

| Number of formula | B | Melting point | Color of Crystal |
|---|---|---|---|
| (35) | 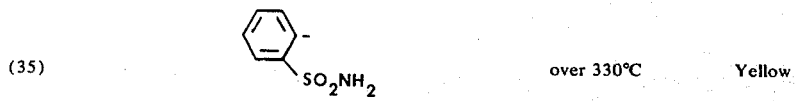 | over 330°C | Yellow |
| (36) |  | over 330°C | Light Yellow |

-continued

| Number of formula | B | Melting point | Color of Crystal |
|---|---|---|---|
| (37) | iso-$C_3H_7NHO_2S$—⟨phenyl⟩— | 272–275°C | Light Yellow |
| (38) | ⟨phenyl⟩—$SO_2N(CH_3)_2$ | 258–263°C | Yellow |
| (39) | $CH_3$-⟨phenyl⟩- with $SO_2NH_2$ | over 330°C | Yellow |
| (40) | Cl-⟨phenyl⟩- with $SO_2NH_2$ | over 330°C | Light Yellow |
| (41) | $H_2NO_2S$-⟨phenyl⟩- with $SO_2NH_2$ | over 330°C | Yellow |

EXAMPLE 4

Added to 100 ml of dimethylformamide were 4.8 g of 4′,4″-diiodo-p-terphenyl, 6.1 g of sodium styrene-o-sulfonate, 3 g of sodium acetate, and 0.01 g of palladous chloride for reaction for 14 hours at a temperature of 150° to 155°C. After cooling, a small amount of insoluble impurity was filtered and the filtrate thus obtained was condensed under a reduced pressure, followed by addition of water, after which the precipitated crystals were filtered and dried, thus obtaining a crude product of 6.3 g. The crude product was recrystallized from a 50% pyridinewater to obtain light yellow crystals of a compound (γ max = 335 mμ) of the formula (42)

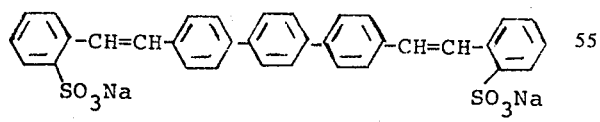

(42)

The starting material, 4′-4″-diiodo-p-terphenyl can be obtained for instance as follows:

Added to a mixture solution of 170 ml of glacial acetic acid and 30 ml of water were 23 g of p-terphenyl, 34 g of potassium persulfate, 25.4 g iodine and 12.6 g of concentrated sulfuric acid, while being refluxed for reaction for 6 hours under heat. After cooling, there followed filtration, washing, drying, thus obtaining 45 g of a crude product. When recrystallized from trichlorobenzene, there was obtained a refined product of white scaly crystals having a melting point of over 350°C.

Reactions were carried out similar to those of the present Example 4, thereby obtaining compounds of the following formula,

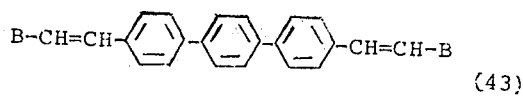

(43)

Those compounds are enumerated as follows:

| Number of Formula | B | λ max | Color of Crystal |
|---|---|---|---|
| (44) | ⟨phenyl⟩-$SO_3NH_2(C_2H_4OH)_2$ | 354 | White |

-continued

| Number of Formula | B | λ max | Color of Crystal |
|---|---|---|---|
| (45) | 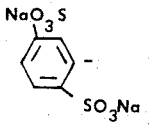 | 357 | Light Greenish Yellow |
| (46) | 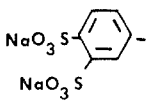 | 357 | Bright Yellow |
| (47) | 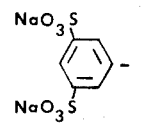 | 355 | Bright Yellow |
| (48) | 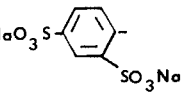 | 357 | Light Yellow |
| (49) | 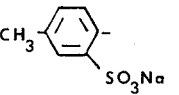 | 358 | Light Yellow |
| (50) | 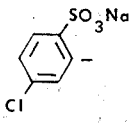 | 356 | Light Yellow |
| (51) | 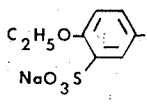 | 371 | Greenish Yellow |

EXAMPLE 5

Added to 100 ml of dimethylformamide were 9.6 g of 4′,4″-diiodo-p-terphenyl, 4.6 g of styrene, 6 g of potassium acetate, and 0.01 g of palladium black for reaction for 20 hours at a temperature of 150°C. After cooling, there followed filtration and washing with water. Subsequently, the palladium as catalyst was extracted for separation of palladium from the cake thus obtained by using a Soxhlet extractor and using 800 ml of chlorobenzene as a solvent. The chlorobenzene solution was cooled, filtrated and dried, thus obtaining a compound of milky white crystals of a compound having the following formula, the amount thereof being 7.5 g;

(52)

The melting point thereof is over 330°C. A refined product was obtained through recrystallization from dimethylformamide.

$C_{34}H_{26}$ = calculated: C 93.97%; H 6.03%; found: C 93.81%; H 5.97%.

Reactions were carried out similar to those of the present Example 5 and thus compounds of the following formula were obtained:

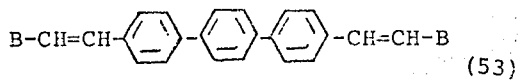

Those compounds are enumerated as follows:

| Number of formula | B | Melting Point | Color of Crystal |
|---|---|---|---|
| (54) | tert-$C_4H_9$–⟨phenyl⟩– | 325–329°C | Light Greenish Yellow |
| (55) | $CH_3O$–⟨phenyl⟩– | over 330°C | Bright Yellow |
| (56) | ⟨phenyl⟩– with Cl | over 330°C | Light Greenish Yellow |
| (57) | $H_2NO_2S$–⟨phenyl⟩– | over 330°C | Light Greenish Yellow |
| (58) | $CH_3$–⟨phenyl⟩– with $SO_2NHC_2H_5$ | over 330°C | Greenish Yellow |

$C_{28}H_{22}$ = calculated: C 93.81%; H 6.19%; found: C 93.70%; H 6.12%.

The starting material, 4,4'-diiodobiphenyl, can be obtained, for instance, as follows:

Added to the mixture solution of 100 ml of glacial acetic acid, 25 ml of water, and 15 ml of carbontetrachloride were 15.4 g of biphenyl, 25.4 g of iodine, 31 g of potassium persulfate, and 7 g of concentrated sulfuric acid, while being refluxed for reaction for 6 hours under heat. 1.5 g of potassium persulfate was added thereto, followed by heating for another 3 hours. After completion of the reaction, there followed cooling, filtration, washing with water and drying, thus obtaining 38 g of a crude product having a melting point of 198° to 202°C. When recrystallized from chlorobenzene, then there was obtained 34 g of white and scaly crystals having a melting point of 201 to 202°C.

Reactions were carried out similar to those of the present Example 6, thus obtaining compounds expressed with the following formula,

EXAMPLE 6

Added to 100 ml of methylcellusolve were 12.2 g of 4,4'-diiodobiphenyl, 6.9 g of styrene, 9 g of potassium acetate, and 0.0054 g of palladous chloride, while being refluxed for reaction for 10 hours under heat. After cooling, there followed filtration, washing with water and drying, after which the palladium serving as catalyst was extracted for separation by using a Soxhlet extractor and using 250 ml of xylene as a solvent. The solution thus extracted was cooled, and then the precipitated crystals were filtered and dried, thus obtaining 9.7 g of a compound of the following formula,

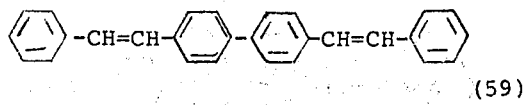

The melting point thereof ranges from 310° to 318°C.

When re-crystallized from dimethylformamide, there were obtained light yellow crystals having a melting point of 325° to 328°C.

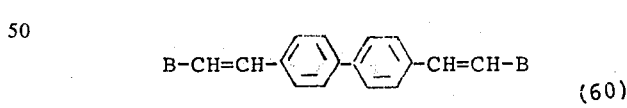

Those compounds are enumerated as follows:

| Number of formula | B | Melting Point | Color of Crystal |
|---|---|---|---|
| (61) | $CH_3$–⟨phenyl⟩– | over 330°C | Light Yellow |
| (62) | iso-$C_3H_7$–⟨phenyl⟩– | 312–316°C | Light Yellow |

-continued

| Number of formula | B | Melting Point | Color of Crystal |
|---|---|---|---|
| (63) | CH$_3$-C$_6$H$_3$(SO$_2$NH$_2$)- | over 330°C | Light Yellow |
| (64) | C$_6$H$_5$(SO$_2$NHCH$_3$)- | 231–234°C | Bright Yellow |
| (65) | (CH$_3$)$_2$NO$_2$S-C$_6$H$_3$(SO$_2$N(CH$_3$)$_2$)- | 254–256°C | Yellow |
| (66) | CH$_3$-C$_6$H$_3$(SO$_2$NHC$_3$H$_6$OCH$_3$)- | 208–211°C | Yellow |

EXAMPLE 7

Added to 100 ml of methylcellosolve were 8.1 g of 4.4′-diiodobiphenyl, 9 g of sodium styrene-o-sulfonate, 6 g of potassium acetate, and 0.054 g of palladous chloride, while being refluxed for reaction for 3 hours under heat. After cooling, there followed filtration, washing with 30 ml of methanol, and the cake thus obtained was dissolved in 100 ml of hot water, such that the insoluble palladium was filtered and recovered. The filtrate was then cooled, salted out with 10 g of sodium chloride, filtered and dried, thus obtaining a compound of the following formula and of light yellow crystals:

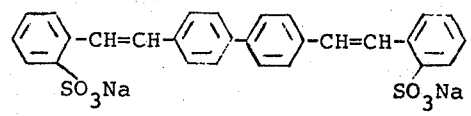

(67)

The yield was 9.3 g.

Methylcellosolve was recovered by distillation from the initial filtrate, after which potassium iodide could be recovered from the residue thus obtained.

When, in place of the sodium styrene-o-sulfonate of the present Example 7, sodium styrene-o-sulfonate containing 20% each of m-isomer and p-isomer is used which has been obtained by removing least aqueous p-isomer from the isomers of styrene-sulfonic acid that have been obtained after sulfonization of chloroethylbenzene, followed by elimination of hydrogen-chloride with alkali, then there will be obtained 8.4 g of a product containing as a principal component a compound of the formula (67) and isomers presenting properties equivalent to those of a compound of the formula (67).

Reactions were carried out similar to those of the present Example 7, thus obtaining compounds of the following formula (68).

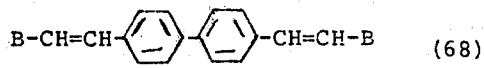

(68)

Those compounds are enumerated as follows:

| Number of formula | B | λ max | Color of Crystal |
|---|---|---|---|
| (69) | C$_6$H$_4$(SO$_3$Na)- | 349 mμ | Light Yellow |
| (70) | CH$_3$-C$_6$H$_3$(SO$_3$Na)- | 353 | Light Greenish Yellow |
| (71) | CH$_3$-C$_6$H$_3$(SO$_3$Na)- | 352 | Light Greenish Yellow |

-continued

| Number of formula | B | λ max | Color of Crystal |
|---|---|---|---|
| (72) | CH₃O-⟨⟩- with SO₃Na | 362 | Greenish Yellow |
| (73) | Cl-⟨⟩- with SO₃Na | 349 | Light Greenish Yellow |
| (74) | NaO₃S-⟨⟩- with SO₃Na | 352 | Bright Yellow |
| (75) | NaO₃S, NaO₃S disubstituted phenyl | 351 | Light Yellow |
| (76) | NaO₃S-⟨⟩- with SO₃Na | 350 | Light Yellow |
| (77) | NaO₃S-⟨⟩- with NaO₃S | 350 | Light Greenish Yellow |

EXAMPLE 8

Added to 100 ml of dimethylformamide were 9 g of 4.4′-dibromobiphenyl, 9.3 g of 4-methoxystyrene, 9 g of potassium acetate and 10.8 g of palladous chloride for reaction for 6 hours at the temperature of 150°C. After cooling, there followed filtration, washing with water and drying. Subsequently, extraction was carried out by using a Soxhlet extractor and using 250 ml of xylene as a solvent. The xylene extract was cooled, filtered and dried, thus giving 6.9 g of a compound of greenish yellow crystals having a melting point of over 330°C and of the following formula:

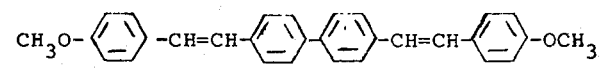

(78)

EXAMPLE 9

Added to 140 ml of ethylcellosolve were 8.4 g of 4.4′-diiodofluorene, 4.2 g of sodium styrene-m-sulfonate, 6 g of potassium acetate, and 0.07 g of palladous chloride for reaction for 2 hours at a temperature of about 120°C. Then, 6.6 g of sodium styrene- 2.4-disulfonate was added thereto for reaction for 2 hours under reflux. After cooling and filtration, the cake thus obtained was dissolved in 100 ml of water. The insoluble palladium was filtered for separation and recovered, while the filtrate was salted out, and the precipitated crystals were filtered and washed with a small amount of salt water and dried, thus obtaining 8.9 g of a product consisting principally of a compound of the following formula;

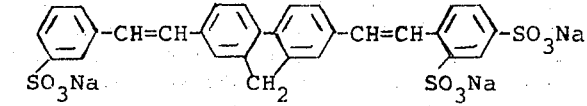

(79)

The product was crystals and exhibited yellow color and presented γ max = 374 mμ in an aqueous solution.

Likewise, compounds of the following formulae were obtained:

| Number of formula | | λ max | Color of crystal |
|---|---|---|---|
| 80 | ⟨⟩-CH=CH-⟨⟩⟨⟩-CH=CH-⟨⟩ with SO₃Na, CH₂, SO₃Na | 373 mμ | Light yellow |
| 81 | ⟨⟩-CH=CH-⟨⟩⟨⟩-CH=CH-⟨⟩ with CH₂, SO₃K | 372 mμ | Light yellow |
| 82 | Cl-⟨⟩-CH=CH-⟨⟩⟨⟩-CH=CH-⟨⟩ with CH₂, SO₃Na | 373 mμ | Light yellow |

| Number of formula | | λ max | Color of crystal |
|---|---|---|---|
| 83 | (structure: Cl-C6H4-CH=CH-C6H4-CH2-C6H4-CH=CH-C6H4-SO3Na) | 371 mμ | Light yellow |
| 84 | (structure: (SO3Na)C6H4-CH=CH-C6H4-C6H4-C6H4-CH=CH-C6H3(SO3Na)-SO3Na) | 356 mμ | Light greenish yellow |

EXAMPLE 10

Added to 100 ml of water were 0.004 g of a compound of the formula (22), (26), (42), (48) or (49) and 0.06 g of sodium sulfate in which was immersed 2 g of a cotton napkin at a temperature of 30°C for 30 minutes. Subsequently, after washing with water and drying, there was obtained slightly red but clearly whitened cloth which presented fairly good light fastness. In this instance, if sodium hypochloride is added for a similar treatment so as to give 100 ppm of effective chlorine concentration, then there will be obtained further excellent whitening effect.

EXAMPLE 11

Added to 100 ml of water was 0.004 g of a compound of the formula (22), (42), (45) or (81), and further added thereto was acetic acid so as to give a pH of 3. 2 g of nylon cloth was immersed therein at a temperature of 60°C, followed by treatment for 40 minutes at a temperature of 90°C. After washing with water and drying, there was obtained a nylon cloth with high whiteness and good light fastness.

EXAMPLE 12

Added to 1000 ml of water were 2 g of synthetic detergent (a mixture of 33 g of sodium dodecylbenzene sulfonate, 31 g of sodium tripolyphosphate, 5 g of sodium silicate, 1 g of carboxymethylcellulose and 30 g of sodium sulfate anhydride), and 0.01 g of a compound of the formula (22), (26), (42), (49) or (80), in which was immersed 20 g of a cotton napkin for 30 minutes, followed by washing, water-rinsing and drying, thus achieving an excellent whitening effect.

EXAMPLE 13

10 g of glyoxal resin was dissolved in 100 ml of water. Added to the solution thus prepared were 1.5 g of zinc nitrate catalyst and 0.2 g of a compound of the formula (22). A bleached cotton broad cloth was immersed therein and squeezed at a squeezing rate of 70%. After drying at a temperature of 70°C for 10 minutes, a heat treatment at a temperature of 150°C for 3 minutes followed. After soaping and drying, there was obtained a cloth having good wrinkling resistance and excellent brightness.

EXAMPLE 14

100 g of bleached sulphite pulp was suspended in 3 liters of water. To the solution thus prepared was mixed a solution in which 0.1 g of a compound of the formula (22), (26), (31), (45), (48), (76) or (79) was dissolved in 100 ml of water, followed by agitation for 30 minutes. Then, 2 g of rosin milk and 3 g of aluminum sulfate were added to the solution for sizing according to a known method, and then the solution was diluted with water so as to give an amount of 20 liters, thereby making paper by a known method using a paper machine. The paper thus prepared exhibited excellent whiteness.

EXAMPLE 15

A polyester woven cloth (Tetron- Toyo Reiyon make) was added to an aqueous dispersing solution at room temperature, said solution container per liter 0.5 g of a compound of the formula (37), 1 g of adduct of about 35 moles of ethylene oxide and 1 mole of octadecyl alcohol. Then, the cloth was squeezed at a squeezing rate of 65%, subjected to drying at a temperature of 70°C for 10 minutes, followed by heat treatment at a temperature of 200°C for 1 minute. After soaping and drying, there was obtained a treated cloth having higher whiteness.

EXAMPLE 16

1 g of a compound of the formula (15) was fused under heat with 2 kg of polystyrene pellets containing titanium dioxide. The fused material thus prepared was extruded through an extruder maintained at a temperature of 210°C, thus obtaining whitened pellets. The pellets thus obtained were placed in an injection type extruder, with the cylinder thereof being maintained at a temperature of 210°C for injection molding, thereby obtaining a polystyrene molded article having a clear milky white color.

If a compound of the formula (16) is used in place of a compound of the formula (15), there will be obtained a slightly bluish whitening effect.

EXAMPLE 17

10 kg of polyamide chip prepared from ε - caparalactam, 30 g of titanium dioxide and 5 g of a compound of the formula (22), (33), (40), (42), (57) or (81) were mixed together in a tumbler for 10 hours. Then, the mixture was melted in an autoclave at a temperature of 260° to 270°C to remove oxygen therefrom, and extruded under nitrogen pressure through a spinning nozzle to thereby obtain a filament stretched by 300%. The filament exhibited an excellent whitening effect.

We claim:
1. A compound of the formula,

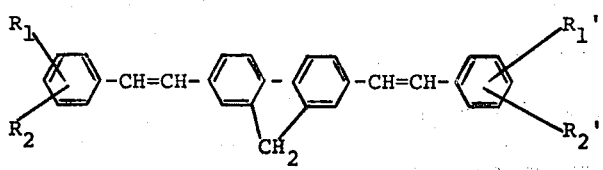

wherein $R_1$ and $R_1'$ may be the same or different, representing a substituent selected from the group consisting of hydrogen, chlorine, lower alkyl, methoxy and ethoxy, and $R_2$ and $R_2'$ may be the same or different, representing a substituent selected from the group consisting of hydrogen, chlorine and lower alkyl.

2. The compound according to claim 1 having the formula,

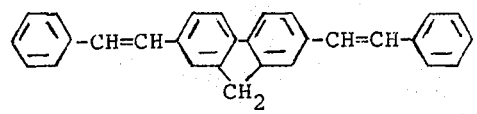

3. The compound according to claim 1 having the formula,

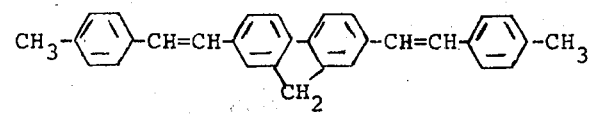

* * * * *